United States Patent [19]
Seaton

[11] Patent Number: 5,092,772
[45] Date of Patent: Mar. 3, 1992

[54] DENTAL PROSTHESES AND CONNECTORS

[76] Inventor: Peter Seaton, 3 Trinity Street, Dorchester, Dorset, Great Britain

[21] Appl. No.: 663,860

[22] PCT Filed: Sep. 8, 1989

[86] PCT No.: PCT/GB89/01057
§ 371 Date: Mar. 13, 1991
§ 102(e) Date: Mar. 13, 1991

[87] PCT Pub. No.: WO90/02531
PCT Pub. Date: Mar. 22, 1990

[30] Foreign Application Priority Data
Sep. 13, 1988 [GB] United Kingdom ............... 8821405

[51] Int. Cl.⁵ ............................................. A61C 13/12
[52] U.S. Cl. ................................... 433/182; 433/181
[58] Field of Search ............... 433/180, 181, 182, 183

[56] References Cited
U.S. PATENT DOCUMENTS
2,705,366 4/1955 Van Dyk ........................ 433/182
3,019,528 2/1962 DePietro .......................... 433/169

FOREIGN PATENT DOCUMENTS
00851126 8/1983 European Pat. Off. ........... 433/181
86/07251 12/1986 PCT Int'l Appl. ................ 433/182

Primary Examiner—John J. Wilson
Attorney, Agent, or Firm—Jones, Tullar & Cooper

[57] ABSTRACT

A dental proosthetic construction is releasably attached at opposite ends to abutment teeth (T). At least at one end, the attachment is by means of a connector comprising a pin (4) and socket (6). The socket has an opening (10) onto the space between the abutment tooth and the prosthesis, the opening continuing over a side of the socket extending longitudinally of the pin. The pin can thus be engaged in the socket by a relative movement transverse to the pin. The pin and socket are then retained in engagement by a releasable latching arrangement (14). The engagement of the pin and socket permits relative translational movement in a direction that varies the spacing between the abutment tooth and the prosthesis but prevents translational movement in other directions. The engagement also permits relative angular movement between the pin and socket about axes transverse to the direction of the relative translational movement but prevents other angular movements.

15 Claims, 4 Drawing Sheets

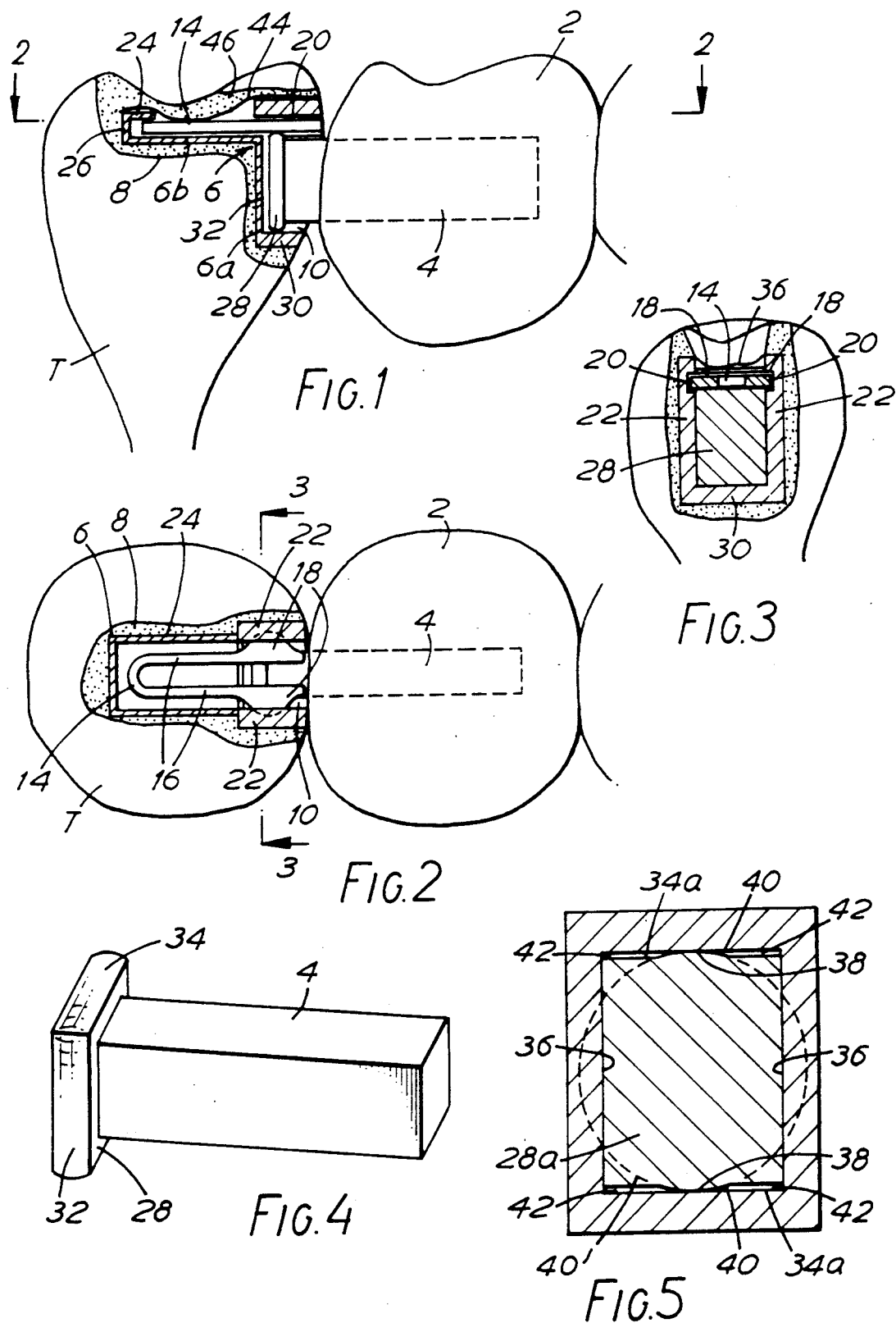

DENTAL PROSTHESES AND CONNECTORS

FIELD OF THE INVENTION

The invention relates to dental prostheses, such as bridges and partial dentures, and in particular to connectors for attaching such prostheses to natural teeth.

DESCRIPTION OF THE PRIOR ART

Prostheses such as a dental bridge or partial denture, comprise an artificial tooth or teeth, known as a "pontic", which extends along the line of the dental arch and is supported on each side by a suitably prepared sound natural tooth, an "abutment tooth". A variety of different connectors are known for securing a pontic to abutment teeth.

The abutment teeth usually have to be prepared by surgery, and in one method they are reduced to parallel sided pillars. A dental bridge is constructed by a technician with caps that fit precisely over the abutment teeth on either side of the pontic, and the bridge is secured using dental cement. This method has a major disadvantage that high bending stresses arise in use on the pontic and the abutment teeth, which are liable to damage the abutment teeth, or may result in the dental cement shearing and the bridge being dislodged. Such bending stresses can arise in the first instance because of imperfections of fit, but even if this is avoided, movements of the abutment teeth, in use, and with the passage of time, give rise to substantial stresses. Of particular importance, of course, are the occlusal loadings that are applied in mastication and there have been many proposals to provide dental prostheses with supports that have stress-breaking capabilities, ie. that reduce these bending stresses.

One arrangement has been proposed (U.S. Pat. No. 1664433) using a crown on the abutment tooth which allows relative vertical movements between the pontic and the abutment tooth, so that direct occlusal pressure can be transmitted to the gums beneath the pontic, but it makes no provision to prevent bending and torsional strains being transmitted to the abutment tooth.

Connectors are also known in the form of pin and socket joints, the pin projecting from the pontic to fit closely in a socket that has been cemented into a cavity formed in the abutment tooth. Such connectors may make it easier to insert and remove the prosthesis, but they can also transmit excessive stresses to the abutment tooth. As examples there may be mentioned U.S. Pat. No. 1,614,325 and U.S. Pat. No. 3,019,528.

In WO 86/07251 I describe pontics having a pin and socket joint. In one case, the pin of the joint has an enlarged head of rectangular cross-section, the edges of that head being formed as cylindrical segments and each opposite pair of edges providing bearing surfaces with a common central axis. In another case, cylindrical segmental bearing surfaces project inwards to engage a prismatic pin. These arrangements permit relative translational movement varying the spacing between the pontic and the abutment tooth as well as pivoting about axes transverse to the direction of said movement, so providing a stress breaking function.

The same patent specification also suggests that a pin and socket joint can employ a pin mounted in the pontic and slidable along its own axis into and out of a socket cemented in an abutment tooth. If this arrangement is combined with a pin and socket joint offering limited rotational freedom as mentioned in the preceding paragraph, there are obtained a number of advantages. There is a limited freedom of displacement of the pin within the socket allowing the pontic and the abutment tooth to move relative to each other, in particular under an occlusal load. The forces transmitted from the pontic to the abutment tooth are reduced, therefore, while the pontic is positively retained in position. Moreover, to the extent that the pin and socket are capable of relative rotational and axial displacement, less skill is required when preparing abutment teeth for the prosthesis, while axial displaceability of the pins allows the prosthesis to be removed and replaced.

There are instances, however, in which the methods of connection using displaceable pins as taught by WO86/07251 cannot be easily applied. Moving a connector pin between extended and withdrawn positions may not always be easy to achieve or control, especially where the pontic is small.

SUMMARY OF THE INVENTION

According to one aspect of the present invention, a dental prosthetic connector for attaching a pontic or other bridge work to an abutment tooth comprises a pin and socket joint for rigid connection one to the pontic and the other to the abutment tooth, the pin having one end that projects into an opening in one side of the socket facing the pontic to fit the socket in a manner permitting relative translational movement in a direction that varies the spacing between the pontic and the abutment tooth and relative angular movement about axes transverse to the direction of said translational movement, while substantially restraining other translational and angular movements, characterised in that said opening in the socket extends over a further side of the socket in the direction of said translational movement so as to permit said projecting end of the pin to be inserted transversely into the socket, and latching means are provided to retain said end of the pin releasably in the socket with said freedom for translational and angular movements.

In the use of the invention, the socket may be embedded in an abutment tooth in a cavity so as to have the opening extending into the occlusal surface of the tooth, or possibly into the side of the tooth. It may be appropriate for the opening to extend into the occlusal surface of a molar or pre-molar, whereas for an incisor or canine it may be preferred to have the opening on the lingual side of the tooth where it is hidden. The latching means may be a discrete member attached separately after the end of the pin has been inserted laterally through the opening and into the socket, or it may be carried by the pin or the socket, e.g. as a sprung projection that engages automatically when the end of the pin enters the socket.

According to another aspect of the invention, there is provided a dental prosthetic construction comprising a pontic or other bridge work, and means for connecting opposite ends of said pontic to respective abutment teeth, at least at one end said means being in the form of a connector comprising a pin and socket joint for rigid connection one to the pontic and the other to the adjacent abutment tooth, the pin having one end that projects into an opening in one side of the socket facing the pontic to fit the socket in a manner permitting relative translational movement in a direction that varies the spacing between the pontic and the abutment tooth and relative angular movement about axes transverse to the direction of said translational movement, while substantially restraining other translational and angular movements, characterised in that said opening in the socket extends over a further side of the socket in the direction of said translational movement so as to permit said projecting end of the pin to be inserted transversely into the socket, and latching means are provided to retain said end of the pin releasably in the socket with said freedom for translational and angular movements.

A pontic, or other bridge work, may be secured by a similar pair of connectors, with respective pins projecting oppositely from its two ends for insertion through into the sockets provided in abutment teeth. Alternatively, in certain circumstances the connector at one end may be arranged to permit rotation about the associated axis of said translational movement, the rotational restraint being assumed at a single end of the pontic. In either case, preferably the open sides of both openings through which the ends of the pins are inserted face in the same direction.

BRIEF DESCRIPTION OF THE DRAWINGS

Embodiments of the invention are now described by way of example only and with reference to the drawings, wherein:

FIG. 1 shows a cross-section through a connector according to a first embodiment;

FIG. 2 is a plan view of the connector partly sectioned on 2—2 in FIG. 1;

FIG. 3 shows a section on 3—3 in FIG. 2;

FIG. 4 is an oblique view of a pin of the connector of FIGS. 1 to 3,

FIG. 5 illustrates a modification of the head of the pin in FIG. 4,

DESCRIPTION OF PREFERRED EMBODIMENTS

Figure 6:
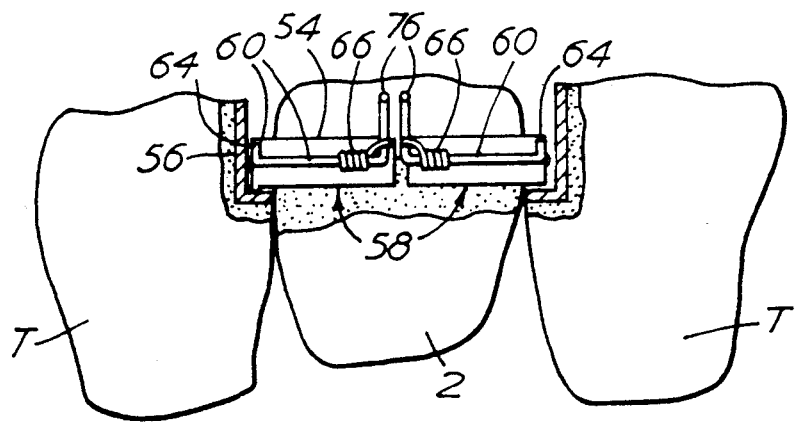
FIGS. 6 is a partly sectional side view of a second embodiment of the invention.
Figure 7:
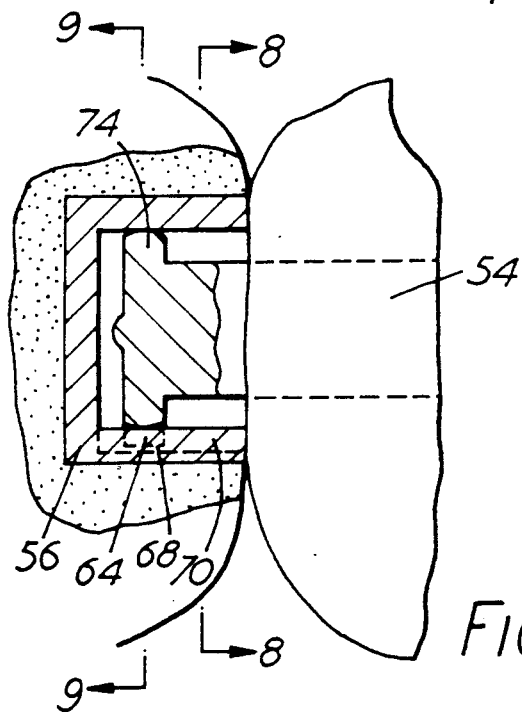
FIG. 7 is a detail plan section of a part of the connector shown in FIG. 6.
Figure 8:
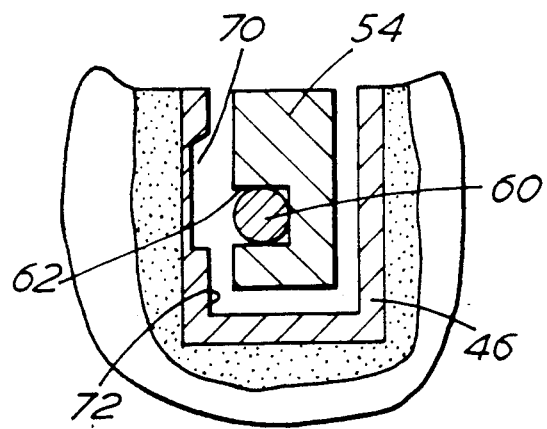
FIG. 8 is a sectional view on 8—8 in FIG. 7, FIGS. 9 and 10 are sectional views on 9—9 in FIG. 7 showing the unlatched and latched positions respectively.

FIGS. 1 to 3 show an abutment tooth T and a pontic 2 linked by a connector which comprises a pin 4 fixed in the pontic and an L-shaped socket 6 secured to the abutment tooth by filler material 8. The socket 6 has an opening 10 extending over the side facing the pontic and continuing over the side directed towards the occlusal surface of the abutment tooth. One end of the pin projects into a relatively deep region 6a of the socket nearest the pontic. A shallower region 6b of the socket continues further away from the pontic and into it projects a latch member in the form of a spring clip 14 which retains the end of the pin 4 in the socket.

The clip 14 has an elongated U-form, with limbs 16 that have lateral enlargements 18 near their free ends. The socket 6 has grooves 20 in its side walls 22 to engage the enlargements and a lip 24 projecting from its end wall 26 to engage the curl of the clip. The clip is therefore positively locked against removal through the open upper face of the socket but can easily be inserted and removed if the limbs 16 are squeezed together.

The pin 4 has an oblong cross-section and the end projecting into the socket 6 has an enlarged head 28 that fits closely the socket side and bottom walls 22,30 and the bottom face of the spring clip 14, but can slide on these surfaces in a direction that varies the spacing between the abutment tooth and the pontic. As can be seen from FIG. 4, the side edges 32,34 of the head 28 are of arcuate cylindrical form, with an axial centre midway between each opposite pair of faces. The head can therefore pivot relative to these sockets about each of these axial centres, as well as slide axially of the socket. Any sensible rotation about the axis of the pin 4 or translational movement other than axially of the pin is prevented, however.

In theory, an exact fit between the side faces the head 28 and the opposed faces 36,38 of the socket and clip would prevent pivoting about any axis but the two axial centres of the arcuate faces. In practice, the angular movements demanded are so small that there is sufficient freedom for compound angular movements about both axes simultaneously while still retaining an effective restraint against pivoting about the axis of the pin. If it should be found in any particular case that greater freedom is required, a modified form of head 28a, as shown in FIG. 5, can be employed. One pair of side faces 34a has its end margins relieved to give acting bearing surfaces 40 that are portions of a spherical envelope 40'. The side margin clearances 42 are much exaggerated in the figure for illustration only.

When the pontic of FIGS. 1 to 3 is to be fitted, the abutment tooth T is prepared to receive the socket 6, which is cemented firmly in place, whereupon the pontic with its pin 4 can be simply dropped into position, the projecting end of the pin being able to enter the socket through the opening in the occlusal surface of the tooth. The spring clip 14 is then located in the socket, under the lip 24 and in the grooves 20, to latch the pontic in place. It will also be understood that its limbs can be sprung together by a suitable tool to release it again should it be needed to remove the pontic at any time.

Although the pontic is locked in place by the connector, the pivoting and sliding freedoms between the pin and the socket as described allow some relative movement to take place so that loadings occurring in mastication, and bending loads in particular, can be at least mainly isolated and not transferred from the pontic to the abutment tooth. The cross-sectional form of the pin and socket ensure, nevertheless, that the pontic remains in appropriate alignment.

The latched connection between the pontic and the abutment tooth clearly makes it relatively easy to put the prosthesis in place and to remove it, if required later for repair. To the patient there is the considerable benefit of limiting the transfer of stresses from the pontic to the abutment tooth, bringing increased comfort in use and less risk of damage.

It may be desired to hide the presence of the connector in the occlusal surface of the abutment tooth. FIGS. 1 and 3 illustrate how a membrane 44 can be laid in the occlusal surface over the socket 6 and filler material 46 added to fill in the cavity above the membrane. The membrane ensures that filler material will not penetrate into the socket so as to block movements of the pin in the socket. It will be understood that the filler material can be drilled out and the membrane removed if it is required to regain access to the socket for further work on the prosthesis.

An alternative embodiment of the invention is illustrated in FIGS. 6 to 10 in which the connector between a pontic 2 and each abutment tooth T comprises pin 54 having an enlarged head similar to that already described engaged in a socket 56. For each pin and socket connection there is a retaining latch 58 comprising a shaft 60 pivotally mounted in a slot 62 in its pin and an integral bit 64 projecting from the shaft at the head of the pin. A spring 66 acts on the shaft to rotate it to a position in which the bit projects laterally from the head of the pin. The top edge 68 of the bit has an arcuate profile perpendicular to the drawing plane of FIGS. 9 and 10. In the projecting position of the bit the edge 68 is engaged by an axial slot 70 in side wall 72 of the socket and functions in conjunction with the bottom edge of head 74 of the pin 54 as a pivot bearing, similarly to the edges 34 of the pin 4 in the first embodiment. In other respects, the engaging faces of the head 74 of the pin in the socket can be formed in the same way as described in that first embodiment.

Figure 9:
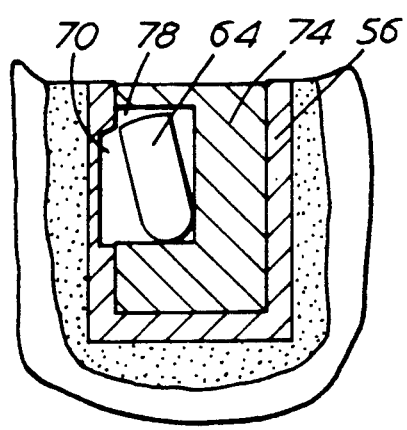
Figure 10:
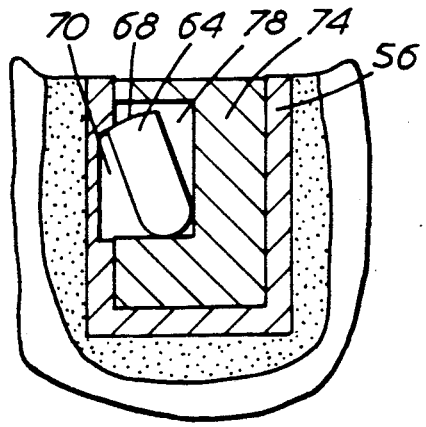

To move the latch 58 against the spring 66, an arm 76 projects from the shaft 60. The arm is placed in the pontic where it can be manipulated to pivot the bit from the slot 70 into recess 78 in the head of the pin, as shown in FIG. 9. When the pontic is put in place and the arm released, the bit springs into the position shown in FIG. 10; the pin is locked in the socket but without affecting the freedom for relative rotation between the abutment tooth and the pontic about axes transverse to the axis of the shaft, nor the freedom for longitudinal sliding movement. In principle, the bit should not bear against the vertical side of the slot as this would create resistance to the required freedom of movement, but if the bearing force is small the loss of efficiency would be negligible.

In FIGS. 11 to 15 a further connector is shown, in this case with a latch that is external to both the pin 54 in the pontic 2 and the socket 56 in the abutment tooth T. To latch the prosthesis in place, the pontic now carries a pair of arms 80 mounted on pivots 82 to be able to swing laterally outwardly, away from the pontic. The socket is formed with a pair of opposite, lateral top flanges 84 and the arms carry upwardly projecting posts 86 the top faces 88 of which engage the undersides 90 of the flanges when the arms are swung inwards. In this engagement position the main part of the arms are located in recesses 92 to lie flush with the pontic. The arms 80 can be held frictionally in their engaged positions or can be positively locked to the sides of the pontic by locking means (not shown).

Figure 11:
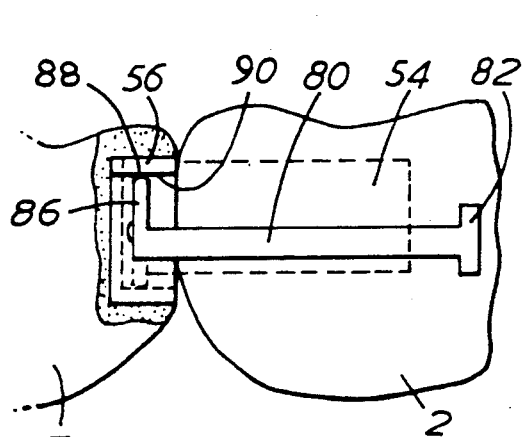
FIG. 11 is a sectional side view of a third embodiment of the invention.
Figure 12:
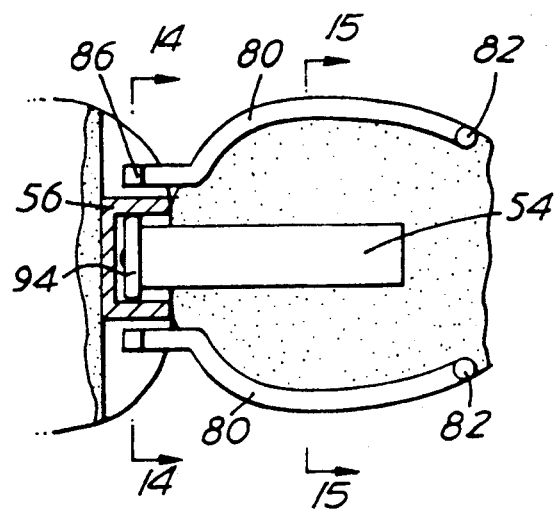
FIGS. 12 and 13 are plan sectional views of the connector of FIG. 11 in the latched and unlatched conditions respectively.
Figure 13:
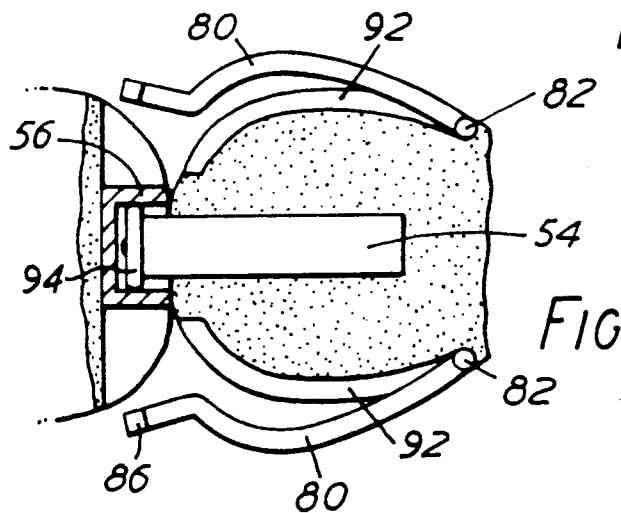
Figure 14:
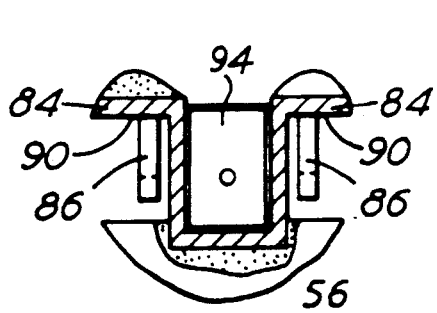
FIGS. 14 and 15 are sectional views on 14—14 and 15—15 respectively in FIG. 12.
Figure 15:
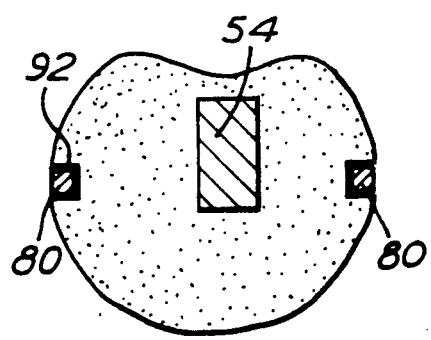

The top faces 88 of the posts 86 have an arcuate profile as seen in FIG. 11 and in combination with the curved bottom edge of head 94 of the pin, a pivot bearing is provided, similarly to the edges 34 of the pin 4 in the first embodiment, in this case supported on one side against the flanges 84 and on the other side against the bottom wall of the socket. Although a pair of latching arms are shown, it is possible in many cases to secure the connection in a similar way with a single arm.

Figure 16:
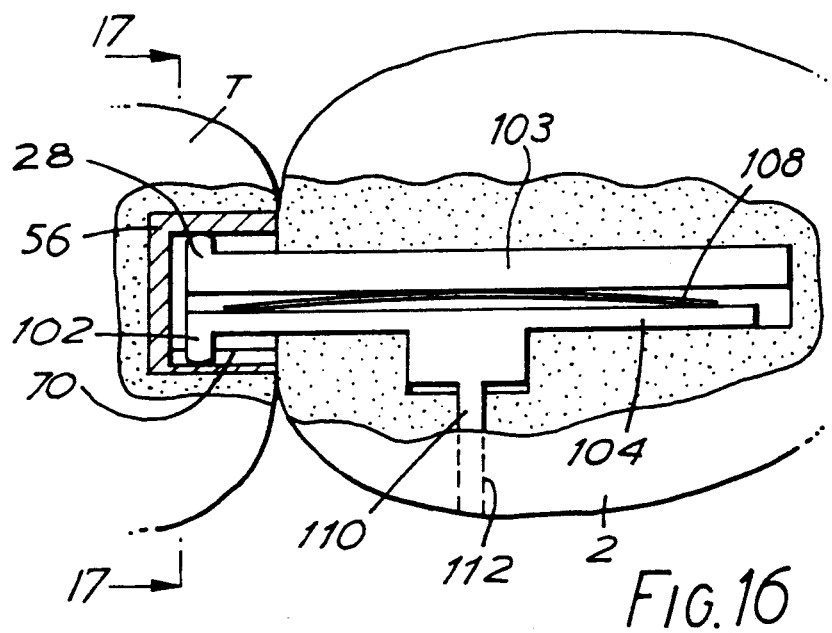
FIG. 16 is a top plan view of a further embodiment of the invention.
Figure 17:
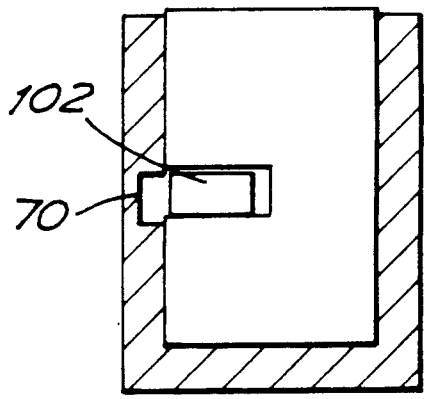
FIGS. 17 and 18 are sectional views on 17—17 in FIG. 16 showing the connector in the unlatched and latched conditions respectively.
Figure 18:
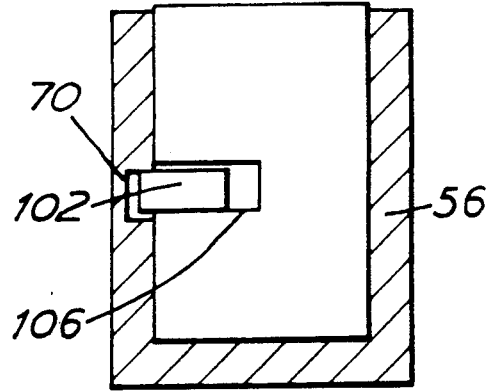

In FIGS. 16 to 18 a further connector is shown comprising a latch 102 held by a pin 103 in the pontic 2 and retaining the enlarged head of the pin in a socket. The head and socket are identified by the references 28,56 because they are essentially identical to the head 28 and socket 56 already described. The latch 102 is integral with a bar 104 that can enter a longitudinal groove 106 in the pin and is urged outwards from the groove by a leaf spring 108. A plunger 110 is formed on the arm to project transversely through a guide bore 112 in the pontic. By depressing the plunger with a tool (not shown), the bar 104 is pushed into the groove 106 against the spring bias and the latch 102 is disengaged from the slot 70 in the socket. This is the position shown in FIG. 17.

When the plunger is released, the latch 102 is again pushed into the slot 70 by the force of the spring 108, as shown in FIG. 18. In this position the engagement between the pin and the socket is kinematically equivalent to the systems already described, with pivoting about an axis transverse to the section plane 17—17 being prevented while pivoting can take place about axes in that plane.

Of course, in these later examples the presence of the socket may be disguised in the crown of the tooth using a membrane or like shield and filling in the manner already described in the example of FIGS. 1 to 3. It is alternatively possible in each embodiment to have an open face of the socket in the side wall of the abutment tooth, in particular in the lingual side, so that the occlusal surface is left intact. The latching means would of course then be reoriented to prevent movement of the pin out of that open side recess. It may be appropriate for the socket to open into the occlusal surface of a molar or premolar, whereas for an incisor or canine it may be preferred to hide the socket on the lingual side of the tooth.

Figure 19:
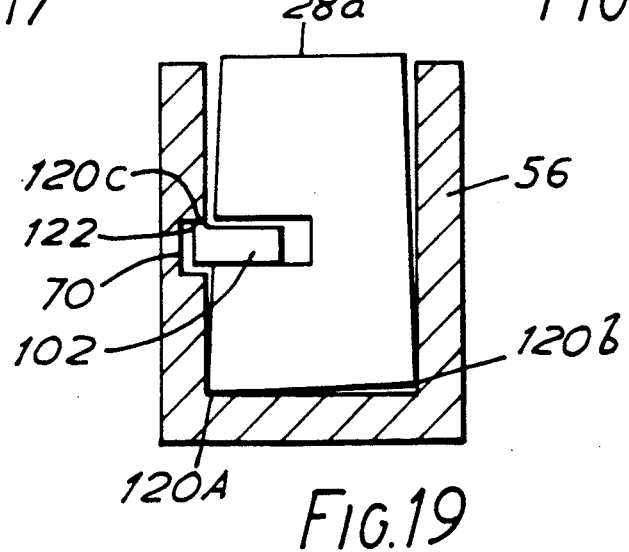
FIG. 19 illustrates a modification of the last-described embodiment.

As has already been indicated, a dental prosthetic construction according to the invention may have its rotational movement limited only at one end. In all the preceding examples, therefore, the pontic may have at its unillustrated end a connector different from the form of connector described. FIG. 19 shows schematically a modification of the connector of FIGS. 16-18 that would provide the additional freedom of movement. The profile of the head 28a of the pin 104 and/or facing sides of the socket 56 are so modified that in the transverse section shown in FIG. 18 the socket and of the head of the pin have three contact points 120a,120b,120c-at the lower corners of the head 28a, and between the latch 102 and its slot 70, and the latch contacting the slot through a convex tip 122. Pivoting can thus take place about the contact point between the latch and its slot.

It will be appreciated that different shapes of sockets may be used for connectors according to the invention as may different shapes of pin. As described in WO86/07251, for example, the tilting engagement between the pin and the socket can be provided by convex faces on the socket rather than the pin. It is not necessary for the pin to be embedded in the pontic and the socket in the abutment tooth; the pin and socket could be located in abutment tooth and pontic respectively, although this arrangement requires more drilling and removal of healthy tooth than is needed in the illustrated embodiments.

Other forms of latching means may be provided, not necessarily employing resilient elements, arranged to be disposed wholly within the socket or pin and socket, or relying additionally on an engagement at a location spaced from the pontic and abutment tooth. Also, while examples have been shown of displaceable latching elements attached to the pin or the pontic, it is possible for such elements to be carried by the socket instead, eg. the positions of the latch bit 64 and socket 70 being revised.

Other dental prosthetic structures, such as dentures, may also be attached using connectors made in accordance with the invention.

In WO 86/07251, I described various methods of securing a socket within an abutment tooth, and various materials for use in making any parts required This information is incorporated herein by reference.

What is claimed is:

1. A dental prosthetic connector for attaching a dental prosthesis to an abutment tooth, comprising a pin and socket joint for rigid connection of the prosthesis to the abutment tooth, said pin having a first end that projects into an opening in a first side of said socket facing the prosthesis to fit the socket in a manner permitting relative translational movement in a direction that varies the spacing between the prosthesis and the abutment tooth and relative angular movement about axes transverse to the direction of said translational movement, while substantially restraining other translational and angular movements, said opening in said socket extending over a second side of said socket in the direction of said translational movement so as to permit said projecting first end of said pin to be inserted transversely into said socket, and releasable latching means provided to retain said first end of said pin releasably in said socket with said freedom for translational and angular movements.

2. A dental prosthesis connector according to claim 1 wherein said latching means comprise at least a first discrete member arranged to be placed in a retaining position after said first end of said pin has been inserted into said socket.

3. A dental prosthesis connector according to claim 2 wherein said latching means is arranged to be placed in said retaining position externally of said socket.

4. A dental prosthesis connector according to claim 1 wherein said latching means comprises an element carried by one of said pin and said socket.

5. A dental prosthesis connector according to claim 4 wherein said latching means comprise a resiliently biassed projection arranged to engage in a latching position under the force of its bias as said pin is inserted into position in said socket.

6. A dental prosthesis connector according to any one of the preceding claims wherein said latching means provides a bearing face for said freedom for translational and angular movement.

7. A dental prosthesis connector according to any one of claims 1 to 5 wherein said first end of said pin has an enlarged cross-section having side faces engaging side faces of said socket for said permitted pivotal movement, said side faces of at least one of said pin and said socket being convex to provide freedom for said movement, and said latching means engaging a portion of at least one of said faces.

8. A dental prosthetic construction comprising a dental prosthesis, and means for connecting opposing ends of said prosthesis to respective abutment teeth, at least one end of said connecting means being a connector comprising a pin and socket joint for rigid connection of the prosthesis to the adjacent abutment tooth, said pin having a first end that projects into an opening in a first side of said socket facing the prosthesis to fit said socket in a manner permitting relative translational movement in a direction that varies the spacing between the prosthesis and the abutment tooth and relative angular movement about axes transverse to the direction of said translational movement, while substantially restraining other translational and angular movements, said opening in said socket extending over a second side of said socket in the direction of said translational movement so as to permit said projecting first end of said pin to be inserted transversely into said socket, and releasable latching means provided to retain said first end of said pin releasably in said socket with said freedom for translational and angular movements.

9. A dental prosthesis construction according to claim 8 wherein said pin is fixed in said prosthesis.

10. A dental prosthesis construction according to claim 8 or 9 wherein said latching means are displaceably retained in said prosthesis.

11. A dental prosthesis construction according to claim 8 or 9 wherein a second end of said connecting means fixes said prosthesis relative to the adjacent abutment tooth.

12. A dental prosthesis construction according to claim 9 wherein said latching means comprise at least a first discrete member arranged to be placed in a retaining position after said first end of said pin has been inserted into said socket.

13. A dental prosthesis construction according to claim 12 wherein said latching means is arranged to be placed in said retaining position externally of said socket.

14. A dental prosthesis construction according to claim 8 wherein said latching means comprises an element carried by one of said pin and said socket.

15. A dental prosthesis construction according to claim 14 wherein said latching means comprise a resiliently biased projection arranged to engage in a latching position under the force of its bias as said pin is inserted into position in said socket.

* * * * *